(12) United States Patent
Garcia et al.

(10) Patent No.: US 7,383,734 B2
(45) Date of Patent: Jun. 10, 2008

(54) SIMULATION OF MAGNETIC FIELD INDUCED VIBRATIONS IN IMPLANTABLE MEDICAL DEVICES

(75) Inventors: Kateri A. Garcia, Albuquerque, NM (US); Robert Hiller, Minneapolis, MN (US); Troy A. Jenison, Minneapolis, MN (US); Bijoyendra Nath, Minneapolis, MN (US); James D. Neville, Maple Grove, MN (US); Craig L. Wiklund, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 117 days.

(21) Appl. No.: 11/342,912

(22) Filed: Jan. 31, 2006

(65) Prior Publication Data

US 2007/0176596 A1    Aug. 2, 2007

(51) Int. Cl.
G01N 27/72    (2006.01)
A61B 5/05    (2006.01)

(52) U.S. Cl. .................................... 73/668; 600/411

(58) Field of Classification Search ................ 600/411; 434/262; 324/318; 73/662, 649; 74/1 SS
See application file for complete search history.

(56) References Cited

U.S. PATENT DOCUMENTS

| | | | | |
|---|---|---|---|---|
| 5,686,836 | A * | 11/1997 | Sasada et al. ................ | 324/244 |
| 5,694,952 | A * | 12/1997 | Lidman et al. .............. | 128/899 |
| 5,722,998 | A * | 3/1998 | Prutchi et al. ................ | 607/30 |
| 5,782,764 | A * | 7/1998 | Werne ......................... | 600/411 |
| 5,882,304 | A * | 3/1999 | Ehnholm et al. ............ | 600/411 |
| 6,580,947 | B1 * | 6/2003 | Thompson ................... | 607/30 |
| 6,580,948 | B2 * | 6/2003 | Haupert et al. .............. | 607/60 |
| 6,839,596 | B2 * | 1/2005 | Nelson et al. ................ | 607/59 |
| 6,937,906 | B2 * | 8/2005 | Terry et al. .................. | 607/63 |
| 7,020,523 | B1 * | 3/2006 | Lu et al. ....................... | 607/27 |
| 7,024,249 | B2 * | 4/2006 | Weisner et al. ............... | 607/60 |
| 7,162,293 | B2 * | 1/2007 | Weiss .......................... | 600/411 |
| 2002/0137014 | A1 | 9/2002 | Anderson et al. | |
| 2003/0137299 | A1 * | 7/2003 | Ham et al. ................... | 324/313 |
| 2003/0216633 | A1 * | 11/2003 | Licato et al. ............... | 600/410 |
| 2004/0051530 | A1 | 3/2004 | Havens et al. | |
| 2005/0085863 | A1 * | 4/2005 | Brodnick et al. ............. | 607/27 |
| 2005/0242804 | A1 * | 11/2005 | Hintz et al. .................. | 324/244 |
| 2006/0001423 | A1 * | 1/2006 | Barbic ......................... | 324/300 |
| 2006/0069420 | A1 * | 3/2006 | Rademacher et al. ....... | 607/141 |

(Continued)

OTHER PUBLICATIONS

Roger Christoph Lüchinger, "Safety Aspects of Cardiac Pacemakers in Magnetic Resonance Imaging", Ph.D Dissertation, Swiss Federal Institute of Technology Zurich (2002).

(Continued)

*Primary Examiner*—Eric F. Winakur
*Assistant Examiner*—Helene Bor
(74) *Attorney, Agent, or Firm*—Daniel G. Chapik

(57) ABSTRACT

A mechanical response of an implantable medical device (IMD) to a first static magnetic field and a first gradient magnetic field slew rate is simulated by exposing the IMD to a second static magnetic field having a magnitude greater than the first static magnetic field and generating a second gradient magnetic field at the IMD such that a product of the second static magnetic field and a second gradient magnetic field slew rate is substantially equal to a product of the first static magnetic field and the first gradient magnetic field slew rate.

18 Claims, 3 Drawing Sheets

U.S. PATENT DOCUMENTS

| | | | |
|---|---|---|---|
| 2006/0173295 A1* | 8/2006 | Zeijlemaker | 600/427 |
| 2007/0010741 A1* | 1/2007 | Gray et al. | 600/434 |
| 2007/0032722 A1* | 2/2007 | Gray et al. | 600/411 |
| 2007/0038074 A1* | 2/2007 | Ritter et al. | 600/411 |
| 2007/0093142 A1* | 4/2007 | MacDonald et al. | 439/676 |

OTHER PUBLICATIONS

Beth A. Schueler, PH.D., et al., "MRI Compatibility and Visibility Assessment of Implantable Medical Devices," Journal of Magnetic Resonance Imaging, 9:596-603 (1999).

* cited by examiner

SIMULATION OF MAGNETIC FIELD INDUCED VIBRATIONS IN IMPLANTABLE MEDICAL DEVICES

BACKGROUND OF THE INVENTION

The present invention relates to implantable medical devices. In particular, the present invention relates to the simulation and testing of magnetic field induced vibrations in implantable medical devices.

In a magnetic resonance imaging (MRI) scanner, a magnet creates a strong magnetic field that aligns the protons of hydrogen atoms in the body. The MRI scanner then exposes the protons to radio frequency (RF) energy, which spins the various protons to produce a faint signal that is detected and subsequently rendered into an image. During this process, a static magnetic field and a time-varying gradient magnetic field are produced. These fields may result in mechanical interactions between an implantable medical device (IMD) and the MRI environment. In particular, interactions between the static magnetic field and the gradient magnetic field produce vibrations in the IMD. The vibration response of the IMD depends on the frequency and magnitude of the gradient magnetic field. The magnitude of the gradient magnetic field varies with position in the MRI scanner.

As MRI scanner technology evolves, the rate of change of the gradient magnetic field will increase to produce more detailed scans of human tissue. As the slew rate of the gradient magnetic field increases, the intensity of the vibration response of the IMD will also increase. Thus, it is important to test the reliability of IMDs in field strengths and slew rates beyond those produced by contemporary clinical MRI scanners to assure that IMDs perform reliably in future generations of clinical MRI scanners.

BRIEF SUMMARY OF THE INVENTION

The mechanical response of an implantable medical device (IMD) to specified static and gradient fields, such as from a magnetic resonance imaging (MRI) scanner, is simulated by exposing the IMD to testing static and gradient fields. The testing static magnetic field is stronger than the specified MRI static magnetic field and the product of the testing static magnetic field and the testing gradient magnetic field slew rate is substantially equal to or greater than the product of the specified MRI static magnetic field and the specified MRI gradient magnetic field slew rate.

DETAILED DESCRIPTION

Figure 1:
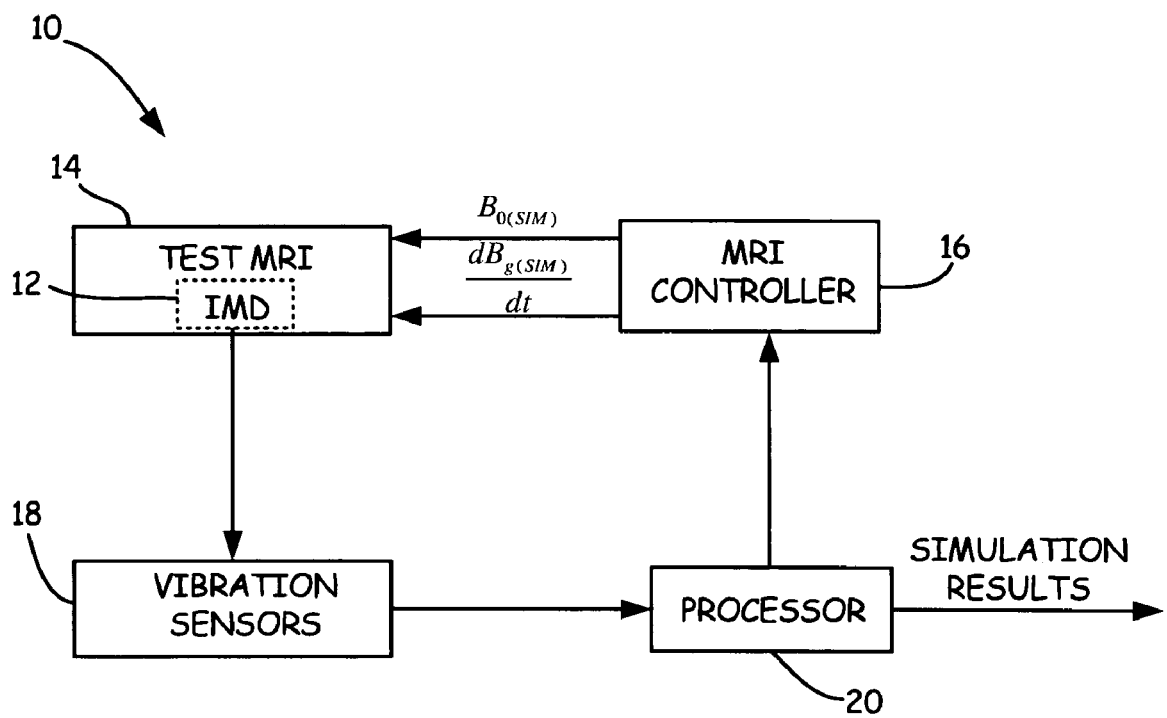
FIG. 1 is a block diagram of a system for simulating and measuring vibrations induced in an implantable medical device (IMD) by a clinical magnetic resonance imaging (MRI) scanner.

FIG. 1 is a block diagram of a system 10 for simulating and measuring magnetic field induced vibrations in an implantable medical device (IMD) 12. System 10 includes test MRI scanner 14, MRI controller 16, vibration sensors 18, and processor 20. IMD 12 (shown in phantom) is disposed within test MRI scanner 14.

Test MRI scanner 14 produces a static magnetic field $B_{0(SIM)}$ and a gradient magnetic field $B_{g(SIM)}$ based on control signals provided by MRI controller 16. The static magnetic field $B_{0(SIM)}$ is a strong one-dimensional magnetic field that is oriented along the longitudinal axis of the bore of test MRI scanner 14. The gradient magnetic field $B_{g(SIM)}$ is a three-dimensional time-varying field that is characterized by the rate of change (i.e., slew rate) of the field, $$\frac{dB_{g(SIM)}}{dt}.$$

Processor 20 controls the operation of MRI controller 16 based on, for example, user input or a testing routine. As will be described in more detail with regard to FIG. 3, the static and gradient magnetic fields generated by test MRI scanner 14 are controlled to simulate vibrations that are induced in IMD 12 in an existing or future-generation clinical MRI scanner. In one embodiment, test MRI scanner 14 is capable of generating a static magnetic field $B_{0(SIM)}$ of at least 5.0 T, such as in the 5.0 T research MRI scanner at the University of Minnesota Center for Interdisciplinary Applications in Magnetic Resonance, Minneapolis, Minn.

When IMD 12 is subjected to the static magnetic field $B_{0(SIM)}$ and the time-varying gradient magnetic field $$\frac{dB_{g(SIM)}}{dt},$$

vibrations are induced in IMD 12 that are measured by vibration sensors 18, which may be internal or external to IMD 12. For example, vibration sensors 18 may include motion sensors in IMD 12 to measure relative motion between the components of IMD 12 and transmit signals related to the sensed motion. The motion sensors may measure the relative velocity, acceleration, and displacement between the components of IMD 12. In addition, a laser interferometer or accelerometer may be disposed relative to IMD 12 to measure the magnitude of the vibration response to gradient magnetic field slew rates $$\frac{dB_{g(SIM)}}{dt}$$

of various frequencies. Signals related to the vibration response of IMD 12 are provided to processor 20, which processes the data and provides the results of the simulation for analysis.

Figure 2:
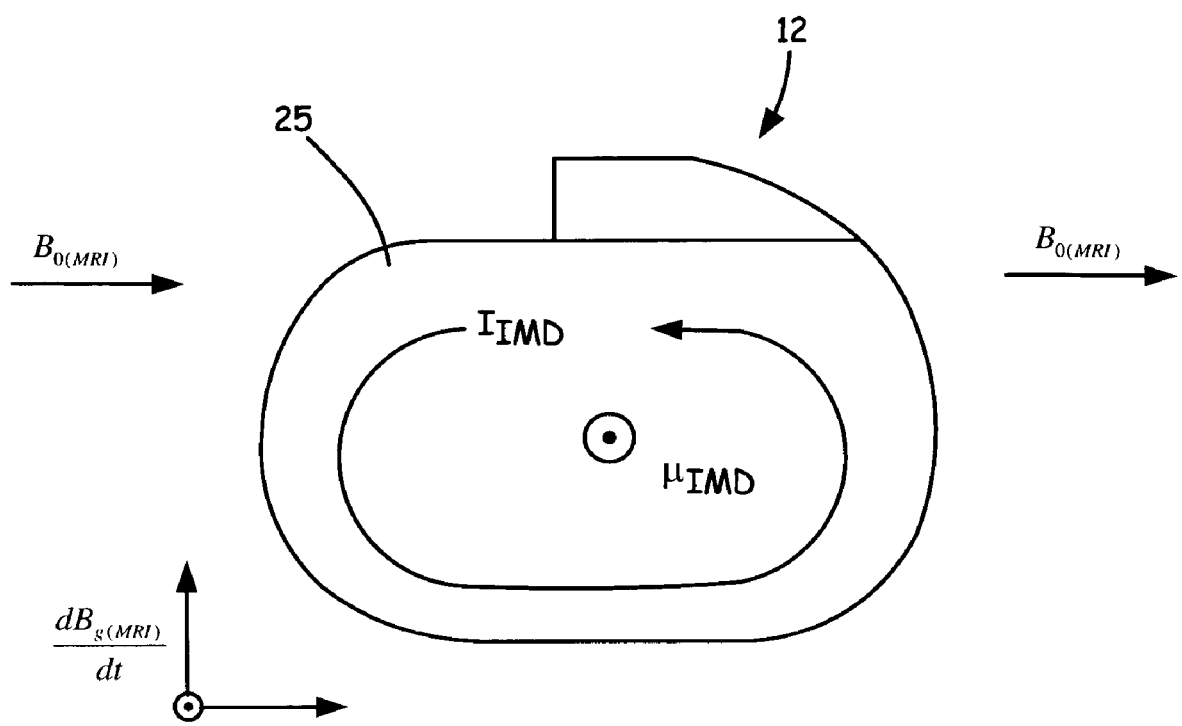
FIG. 2 shows a top view of the implantable medical device disposed in a static magnetic field and a time-varying gradient magnetic field produced in a clinical MRI scanner.

To illustrate the cause of magnetic field induced vibrations in IMD 12, FIG. 2 shows a top view of IMD 12 disposed in a clinical MRI scanner having a static magnetic field $B_{0(MRI)}$ and a gradient magnetic field $B_{g(MRI)}$ with a slew rate of $$\frac{dB_{g(MRI)}}{dt}.$$

In contemporary clinical MRI scanners, static magnetic field $B_{0(MRI)}$ has a magnitude of between about 0.2 T and 3.0 T at the center of the MRI scanner bore, while gradient magnetic field $B_{g(MRI)}$ has a slew rate $$\frac{dB_{g(MRI)}}{dt}$$

of less than about 50 T/s.

IMD 12 includes outer housing 25 made of a conductive material. When IMD 12 is exposed to static magnetic field $B_{0(MRI)}$ and time-varying gradient magnetic field $$\frac{dB_{g(MRI)}}{dt},$$

eddy currents $I_{IMD}$ are induced in conductive housing 25. The eddy currents $I_{IMD}$ produce a magnetic moment $\mu_{IMD}$ oriented perpendicular to IMD 12 given by $$\mu_{IMD} = A_{IMD} I_{IMD} = \frac{A_{IMD}^2}{R} \frac{dB_{g(MRI)}}{dt} \qquad \text{(Equation 1)}$$

where $A_{IMD}$ is the area of the eddy current loops induced in conductive housing 25. In the presence of static magnetic field $B_{0(MRI)}$, a torque $N_{IMD}$ acts on IMD 12 given by $$N_{IMD} = \mu_{MRI} \times B_{0(MRI)} \qquad \text{(Equation 2)}.$$

A force $F_{IMD}$ is also produced on IMD 12 given by $$F_{IMD} = \nabla(\mu_{MRI} \cdot B_{0(MRI)}) \qquad \text{(Equation 3)}.$$

The torque $N_{IMD}$ and the force $F_{IMD}$ on IMD 12 change direction and magnitude as the direction and magnitude of gradient magnetic field $B_{g(MRI)}$ varies at slew rate $$\frac{dB_{g(MRI)}}{dt}.$$

The varying magnitude and direction of the torque $N_{IMD}$ and the force $F_{IMD}$ produce vibrations in IMD 12. As shown by Equations 1, 2, and 3, the magnitude of the torque $N_{IMD}$ and the force $F_{IMD}$ on IMD 12 (and thus the intensity of the vibrations in IMD 12) is proportional to the product of static magnetic field $B_{0(MRI)}$ and the slew rate of the gradient magnetic field $$\frac{dB_{g(MRI)}}{dt} \left( \text{i.e., } B_{0(MRI)} \frac{dB_{g(MRI)}}{dt} \right).$$

Figure 3:
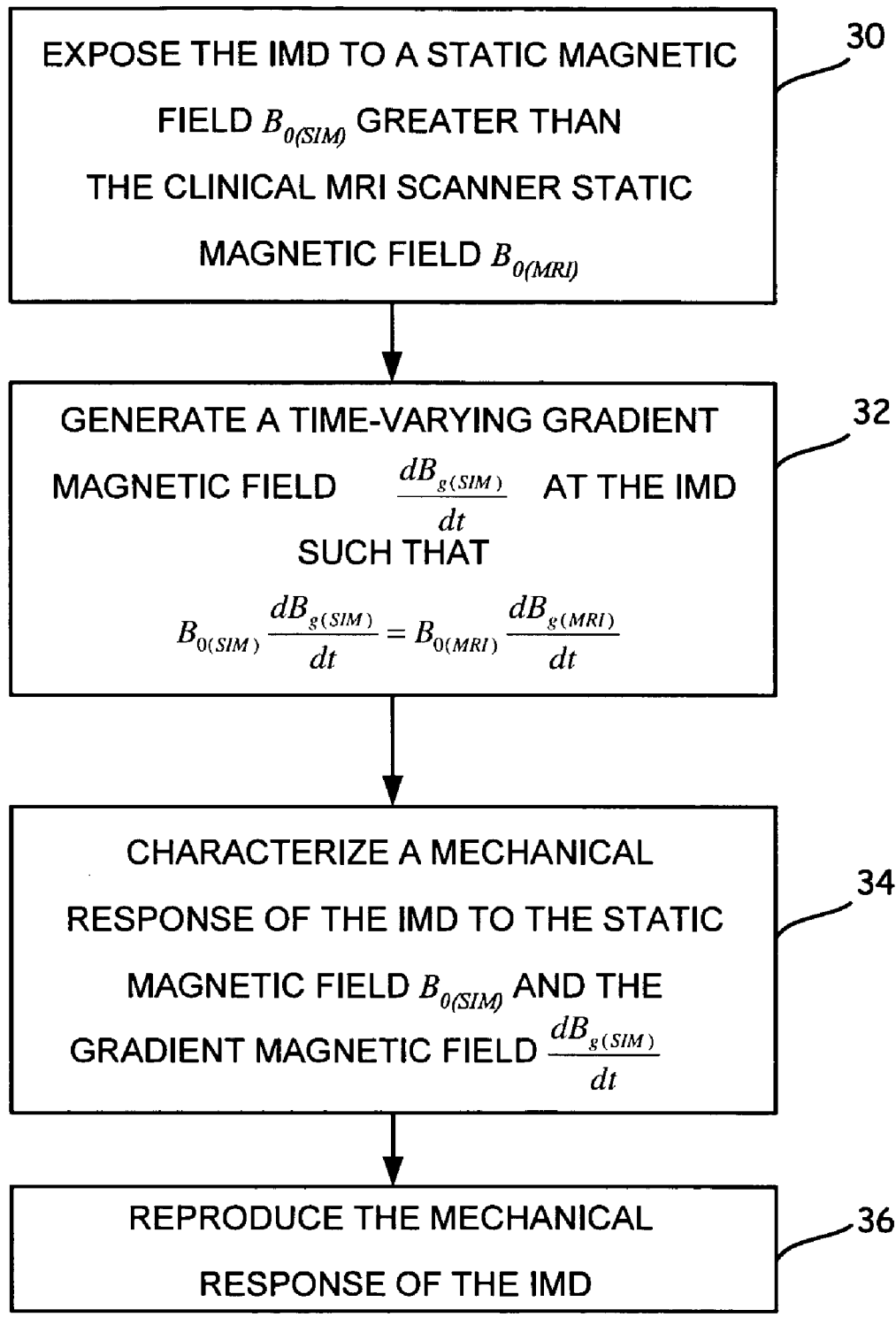
FIG. 3 is a flow diagram showing a method for simulating vibrations induced in an IMD by a clinical MRI scanner.

FIG. 3 is a flow diagram showing a method for simulating vibrations induced in IMD 12 in a clinical MRI scanner having a static magnetic field $B_{0(MRI)}$ and a gradient magnetic field $B_{g(MRI)}$ with a slew rate $$\frac{dB_{g(MRI)}}{dt}.$$

The static magnetic field $B_{0(MRI)}$ and gradient magnetic field slew rate $$\frac{dB_{g(MRI)}}{dt}$$

simulated may be those anticipated in future generations of MRI scanners (e.g., 1.5 T or 3.0 T static magnetic field with a gradient magnetic field slew rate of 100 T/s). IMD 12 is exposed to a static magnetic field $B_{0(SIM)}$ in test MRI scanner 14 that is greater than static magnetic field $B_{0(MRI)}$ from the clinical MRI scanner (step 30). In one embodiment, static magnetic field $B_{0(SIM)}$ has a magnitude of at least 4.0 T.

While IMD 12 is exposed to static magnetic field $B_{0(SIM)}$, the gradient magnetic field $B_{g(SIM)}$ having slew rate $$\frac{dB_{g(SIM)}}{dt}$$

is generated in test MRI scanner 14. The product of the static magnetic field $B_{0(SIM)}$ and the gradient magnetic field slew rate $$\frac{dB_{g(SIM)}}{dt}$$

is substantially equal to the product of the static magnetic field $B_{0(MRI)}$ and the gradient magnetic field slew rate $$\frac{dB_{g(MRI)}}{dt}$$

produced by the current or future generation clinical MRI scanner (step 32). For example, to simulate the vibration response of IMD 12 in an MRI scanner with $B_{0(MRI)} = 1.5$ T and $$\frac{dB_{g(MRI)}}{dt} = 100 \text{ T/s},$$

IMD 12 is placed in test MRI scanner 14 with $B_{0(SIM)} = 5.0$ T and $$\frac{dB_{g(SIM)}}{dt}$$

$= 30$ T/s (i.e., the product of the static magnetic field and the gradient magnetic field slew rate is 150 T²/s). Test MRI scanner 14 may also test IMD 12 in a range of static and gradient magnetic fields (i.e., different values for the product to simulate the vibration response in clinical MRI scanners having various static field strengths and gradient field slew rates. In addition, the frequency of the gradient magnetic field slew rate $$\frac{dB_{g(SIM)}}{dt}$$

may be swept across a range of frequencies to simulate the vibration response of IMD 12 across the same range of frequencies for the clinical MRI scanner gradient magnetic field slew rate $$\frac{dB_{g(MRI)}}{dt}.$$

The amount of time that a patient may be exposed to the time-varying gradient magnetic field $$\frac{dB_{g(MRI)}}{dt}$$

generated by the clinical MRI scanner during each MRI procedure is limited by industry standards, such as International Electrotechnical Commission (IEC) standard 601-2-33. Thus, in order to assure reliability, IMD 12 is exposed to the static magnetic field $B_{0(SIM)}$ and the gradient magnetic field with slew rate $$\frac{dB_{g(SIM)}}{dt}$$

for at least the maximum cumulative exposure time for the clinical MRI gradient magnetic field with slew rate $$\frac{dB_{g(MRI)}}{dt}$$

simulated. IMD 12 may be tested for proper function during and after exposure to the static magnetic field $B_{0(SIM)}$ and gradient magnetic field with slew rate $$\frac{dB_{g(SIM)}}{dt}$$

to assure that IMD 12 performs reliably in the fields tested.

The vibration response of IMD 12 may be characterized to produce data related to the vibrations of IMD 12 (step 34). Vibration sensors 18 measure the vibration response of IMD 12 while exposed to the static magnetic field $B_{0(SIM)}$ and the time-varying gradient magnetic field $$\frac{dB_{g(SIM)}}{dt}.$$

Processor 20 may process the data generated by vibration sensors 18 and produce an output related to the relative motion and frequency response of IMD 12 at the static and gradient field simulated. In addition, processor 20 may perform an analysis of the reliability of IMD 12 in the static and gradient fields in clinical MRI scanners having various static and gradient field characteristics by assessing the vibration response and function for different values for the product $$B_{0(SIM)}\frac{dB_{g(SIM)}}{dt}.$$

The data from vibration sensors 18 may also be used by processor 20 to reproduce the vibration response in IMD 12 (step 36). In one embodiment, the vibration response in IMD 12 is reproduced to test the reliability of a plurality of IMDs 12. To reproduce the vibration response, processor 20 may generate a data profile, such as a power spectral density (PSD) envelope or a fast Fourier transform (FFT) envelope, from the data generated by vibration sensors 18. The data profile may then be used by a device capable of producing controllable mechanical excitations (e.g., a shaker table) to replicate the vibration response of IMD 12. Thus, the vibration response can be reproduced on a group of IMDs 12 for reliability testing without requiring exposure of each IMD 12 to the static magnetic field $B_{0(SIM)}$ and gradient magnetic field $B_{g(SIM)}$ with slew rate $$\frac{dB_{g(SIM)}}{dt}.$$

In summary, the present invention is directed to simulating a mechanical response of an implantable medical device (IMD) to a static magnetic field and a time-varying gradient magnetic field in a clinical MRI scanner. The IMD is exposed to a test static magnetic field having a magnitude greater than the clinical MRI static magnetic field. A test gradient magnetic field is generated at the IMD such that a product of the test static magnetic field and the test gradient magnetic field slew rate is substantially equal to a product of the clinical MRI static magnetic field and the clinical MRI gradient magnetic field slew rate. The mechanical response of the IMD may then be characterized to produce information related to the mechanical response. This information may then be used to reproduce the mechanical response of the IMD to test the reliability of a plurality of IMDs.

Although the present invention has been described with reference to preferred embodiments, workers skilled in the art will recognize that changes may be made in form and detail without departing from the spirit and scope of the invention.

The invention claimed is:

1. A method for simulating a mechanical response of an implantable medical device (IMD) to a first static magnetic field and a first gradient magnetic field slew rate, the method comprising:
   exposing the IMD to a second static magnetic field having a magnitude greater than the first static magnetic field;
   generating a second gradient magnetic field at the IMD, wherein a product of the second static magnetic field and a second gradient magnetic field slew rate is substantially equal to or greater than a product of the first static magnetic field and the first gradient magnetic field slew rate;
   storing data related to the mechanical response produced by the second static and gradient magnetic fields; and
   reproducing the mechanical response based on the stored data.

2. The method of claim 1, wherein the second static magnetic field is at least about 4.0 T.

3. The method of claim 1, wherein the product of the second static magnetic field and the second gradient magnetic field slew rate is at least about 150 $T^2/s$.

4. A method for testing a vibration response of an implantable medical device (IMD) to a first static magnetic field and a first gradient magnetic field slew rate, the method comprising:
   simulating the vibration response by disposing the IMD in a second static magnetic field having a magnitude greater than the first static magnetic field and generating a second gradient magnetic field at the IMD such that a product of the second static magnetic field and a second gradient magnetic field slew rate is substantially equal to or greater than a product of the first static magnetic field and the first gradient magnetic field slew rate; and
   sensing the vibration response of a plurality of components within the the IMD to the second static magnetic field and the second gradient magnetic field.

5. The method of claim 4, wherein the sensing step comprises measuring relative motion between components of the IMD.

6. The method of claim 5, wherein measuring relative motion between components of the IMD comprises at least one of measuring a relative velocity between the components, measuring a relative acceleration between of the components, and measuring a relative displacement between the components.

7. The method of claim 4, and further comprising:
   measuring a magnitude of the vibration response to the second gradient magnetic field at various frequencies.

8. The method of claim 4, and further comprising:
   mechanically reproducing the vibration response to test other IMDs.

9. The method of claim 4, wherein the second static magnetic field is at least about 4.0 T.

10. The method of claim 4, wherein the product of the second static and gradient magnetic fields is at least about 150 $T^2/s$.

11. A method for testing a reliability of a plurality of implantable medical devices (IMDs) in a magnetic resonance imaging (MRI) scanner that generates a first static magnetic field and a first gradient magnetic field, the method comprising:
   exposing an IMD in a second static magnetic field having a magnitude greater than the first static magnetic field;
   generating a second gradient magnetic field at the IMD, wherein a product of the second static and gradient magnetic fields is substantially equal to or greater than a product of the first static and gradient magnetic fields;
   characterizing a mechanical vibratory response of a plurality of components of the IMD to the second static magnetic field and the second gradient magnetic field; and
   reproducing the characterized mechanical vibratory response on the plurality of IMDs.

12. The method of claim 11, wherein the mechanical response is reproduced by a mechanical vibrator.

13. The method of claim 11, wherein the characterizing step comprises measuring relative motion between components of the IMD.

14. The method of claim 13, wherein measuring relative motion between components of the IMD comprises at least one of measuring a relative velocity between the components, measuring a relative acceleration between of the components, and measuring a relative displacement between the components.

15. The method of claim 11, wherein the characterizing step comprises measuring a magnitude of the mechanical response to the second gradient magnetic field at various frequencies.

16. The method of claim 11, and further comprising:
   testing a functionality of the IMDs after reproducing the characterized mechanical response on the plurality of IMDs.

17. The method of claim 11, wherein the second static magnetic field is at least about 4.0 T.

18. The method of claim 11, wherein the product of the second static and gradient magnetic fields is at least about 150 $T^2/s$.

* * * * *